United States Patent [19]
Onik et al.

[11] Patent Number: 5,494,039
[45] Date of Patent: Feb. 27, 1996

[54] BIOPSY NEEDLE INSERTION GUIDE AND METHOD OF USE IN PROSTATE CRYOSURGERY

[75] Inventors: Gary Onik, Allison Park; George Reyes, Pittsburgh, both of Pa.; Larry Pottorff, Candor, N.Y.; Jeffrey Cohen, Pittsburgh, Pa.

[73] Assignee: Cryomedical Sciences, Inc., Rockville, Md.

[21] Appl. No.: 93,020

[22] Filed: Jul. 16, 1993

[51] Int. Cl.⁶ .................................................. A61B 8/00
[52] U.S. Cl. ................................. 128/662.05; 128/749
[58] Field of Search ................................. 128/24 A, 749, 128/754, 662.05; 604/116

[56] References Cited

U.S. PATENT DOCUMENTS

| | | | |
|---|---|---|---|
| 4,576,175 | 3/1986 | Epstein | 128/662.05 |
| 4,742,829 | 5/1988 | Law et al. | 128/660 |
| 4,838,506 | 6/1989 | Cooper | 128/662.05 |
| 4,898,178 | 2/1990 | Wedel | 128/661.05 |

*Primary Examiner*—Max Hindenburg
*Attorney, Agent, or Firm*—Sherman and Shalloway

[57] ABSTRACT

A biopsy needle insertion guide and method of use with an ultrasound probe in medical procedures to accurately position biopsy needles in internal tissues. The insertion guide comprises a body which is removably mountable on an ultrasound probe and which comprises a clamp affixable about the probe and an elongated adjustment guide extending from the clamp in a direction perpendicular to the probe. A slide block engages the adjustment guide and is slidably adjustable therealong and a biopsy needle holder and guide assembly is carried by the slide block and is adjustably extendable from the slide block in a direction parallel to the probe. A method of use is described wherein the insertion guide is used to accurately place biopsy needles in a human prostate, the needles being then used to accurately place cryoprobes in the prostate for cryogenic surgery of the gland.

23 Claims, 4 Drawing Sheets

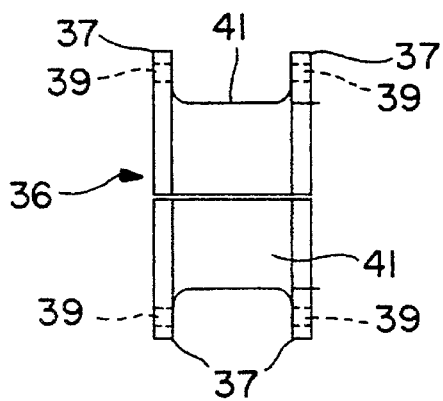 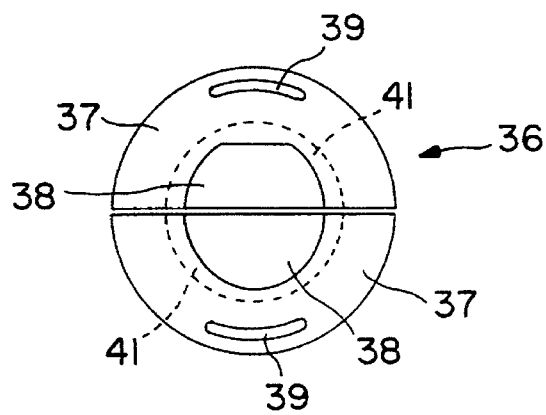
FIG. 12  FIG. 13
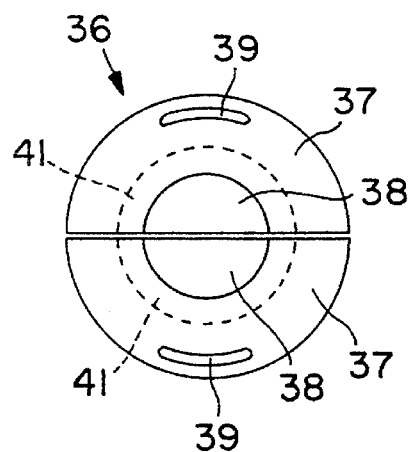 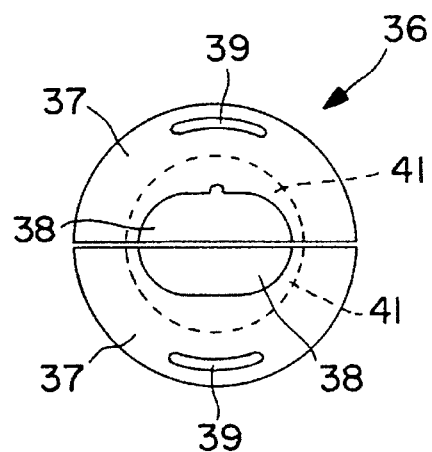
FIG. 14  FIG. 15
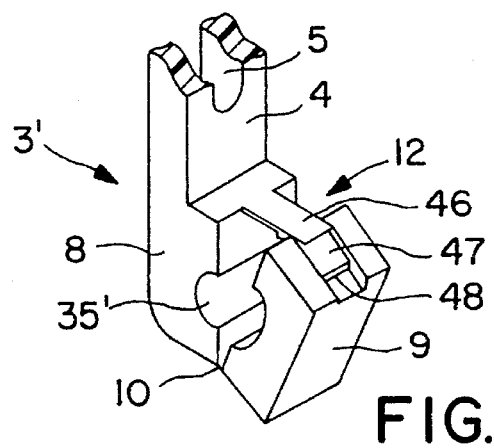
FIG. 16

BIOPSY NEEDLE INSERTION GUIDE AND METHOD OF USE IN PROSTATE CRYOSURGERY

FIELD OF THE INVENTION

This invention relates to prostate cryosurgery and more particularly to a guide for use in achieving accurate placement of cryoprobes within the prostate. Most particularly the invention relates to a biopsy needle insertion guide which is securely mountable on and useable with a rectally inserted ultrasound probe to insert biopsy needles into the prostate at specific target points identified on an ultrasound image of the prostate. The needles provide guidance for placement of cryoprobes within the prostate at those points for cryosurgical treatment of the prostate.

BACKGROUND OF THE INVENTION

Prior treatment of an enlarged and/or tumorous prostate has involved transurethral or transrectal resection of the prostate tissue with the attendant problems associated with such procedures.

In recent years, cryosurgical techniques have been applied to tumorous tissues with considerable success. These techniques succeed in reducing the tissue while avoiding the attendant complications of more conventional surgical techniques. The principal difficulty in applying cryosurgery to internal organs is accurate placement of cryosurgical probes. Generally, imaging techniques are used to provide a visual representation of the desired organ and the surgeon observes the image while he guides probes into place. A popular imaging technique is ultrasound wherein a transducer is placed against the body and transabdominal scans are made to image the internal organs. The image resolution of such scans is limited due to the intervening abdominal tissues, so ultrasound probes which can be inserted into natural body orifices or through cannulas so as to be closer to the target organs are used for deep tissue imaging.

In the case of cryosurgery of the prostate, accurate placement of the cryoprobes is important to control the areal extent of freezing and to avoid damage to surrounding tissues such as the urethra and the rectal wall. This in turn requires high resolution imaging and a way to achieve accurate placement of the cryoprobes relative to the ultrasound probe used to produce the image. Imaging of the prostate is readily obtained by use of an ultrasound probe inserted into the patient's rectum. Because of the proximity of the prostate to the rectum, a high resolution image is obtained and the ultrasound probe can be used as basis from which to gauge probe placement. What is therefor needed is an insertion guide which is securely mountable on the ultrasound probe to provide an adjustable but stable guide which can be used to accurately position biopsy needles within the prostate relative to the ultrasound probe.

Biopsy needle guides which attach to ultrasound probes and transducers for use in positioning needles in tissues being imaged are known as represented by U.S. Pat. No. 4,742,829, Law, et al. U.S. Pat. No. 4,838,506, Cooper, U.S. Pat. No. 4,898,178, Wedel and U.S. Pat. No. 5,052,396. Wedel, et al. However, none of these prior guides provide the combination of adjustability and stability which is necessary to accurately position biopsy needles and, ultimately, cryoprobes in a prostate relative to a rectally inserted ultrasound probe. For example, the device of U.S. Pat. No. 4,742,829 is fixed to a vaginally inserted probe in such a manner that the needle guided thereby is immediately adjacent to the probe so as to extend therealong into tissues located proximally of the probe. No adjustment perpendicular to the probe is available. U.S. Pat. Nos. 4,898,178 and 5,052,396 disclose a needle guide for use with an externally positioned transducer wherein the needle is inserted at a continuously fixed angle relative to the transducer. Adjustment of the position of the needle is limited to its rotary position about the transducer. The device of U.S. Pat. No. 4,838,506 is applicable to an insertable transducer and provides a guide which is adjustable in two dimensions. However, it is of extremely simple construction and does not provide the degree of stability necessary for accurate insertion of biopsy needles and cryoprobes through a patient's perineum and into the prostate.

SUMMARY OF THE INVENTION

It is accordingly an object of this invention to provide an improved biopsy needle insertion guide for use on an ultrasound probe.

It is another objection to provide an improved biopsy needle insertion guide which is securely fixable to a rectally insertable ultrasound probe for use in accurately positioning needles in the prostate of a patient.

It is a further object of this invention to provide an improved biopsy needle insertion guide which is readily adjustable for accurate positioning of needles within body tissues at points radially surrounding an ultrasound probe.

Further objects and advantages will become evident from the following disclosure.

In accordance with this invention there is provided a biopsy needle insertion guide for use with an ultrasound probe in medical procedures, wherein the guide comprises a body removably mountable on an ultrasonic probe and comprising a clamp affixable about the probe and an elongated adjustment guide extending from the clamp in a direction perpendicular to the probe when the body is mounted thereon. The guide further comprises a slide block engaging the adjustment guide and slidably adjustable therealong and a needle holder and guide assembly carried by the slide block and extendable from the slide block in a direction parallel to the probe when the body is mounted thereon.

This structure provides a needle insertion guide which can be mounted on a rectally inserted ultrasound guide used to image a prostate. The insertion guide will rotate relative to the patient when the ultrasound probe is rotated about its longitudinal axis and the slide block is adjustable along the adjustment guide to alter the radial distance of the needle holder and guide from the ultrasound probe. In this manner the entry position of the needle and its position of placement within the prostate is fully adjustable in an anterior-posterior dimension by adjustment of the slide block position, as well as by rotating the ultrasound probe. In addition, the needle holder and guide assembly is adjustable relative to the slide block in a direction parallel to the longitudinal axis of the ultrasound probe in order to engage the perineum of the patient and thereby stabilize the instrument. A spring is provided on this assembly to provide tension against the perineum.

BRIEF DESCRIPTION OF THE DRAWINGS

FIG. 12 is a side view of a sizing insert for the clamp of the insertion guide.

FIG. 13 is a planar view of one embodiment of the sizing insert of FIG. 12.

FIG. 14 is a planar view of another embodiment of the sizing insert of FIG. 12.

FIG. 15 is a planar view of a further embodiment of the sizing insert of FIG. 12.

FIG. 16 is a perspective view of an alternative embodiment of the clamp portion of the insertion guide.

DETAILED DESCRIPTION OF THE INVENTION

Figure 1:
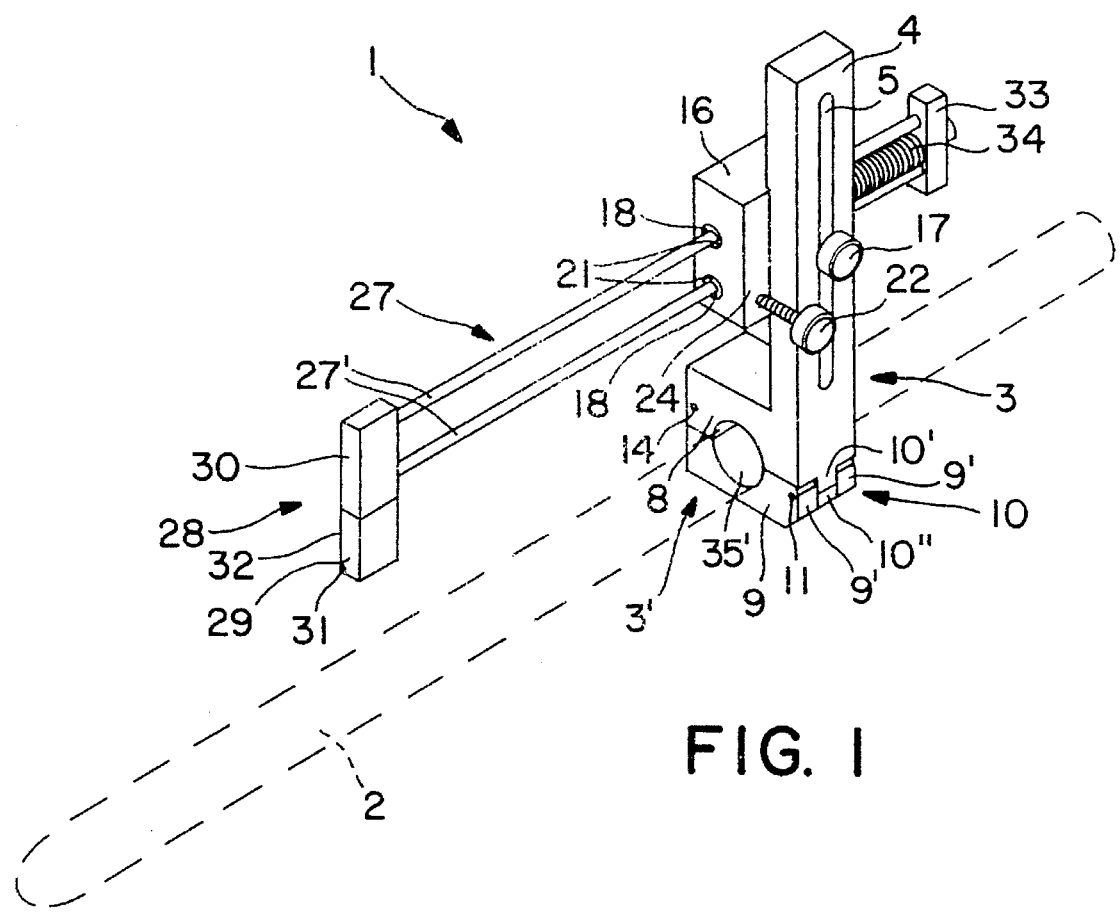
FIG. 1 is a perspective view of the insertion guide mounted on an ultrasound probe.

Looking at FIG. 1 the biopsy needle insertion guide 1 is shown in conjunction with a representative ultrasound probe 2 shown in phantom. Insertion guide 1 includes a main body portion 3 which is made up of an elongated anterior-posterior adjustment guide 4 extending upward from a first clamp body 8. In this embodiment first clamp body 8 forms the upper portion of a clamp 3' whereby insertion guide 1 is removably mountable to ultrasound probe 2. A second clamp body 9 is hingably connected to first clamp body 8 and forms the lower portion of clamp 3'. In an alternative embodiment, illustrated in FIG. 16, first and second clamp bodies 8 and 9 form left and right sides of the clamp 3' respectively.

Figure 4:
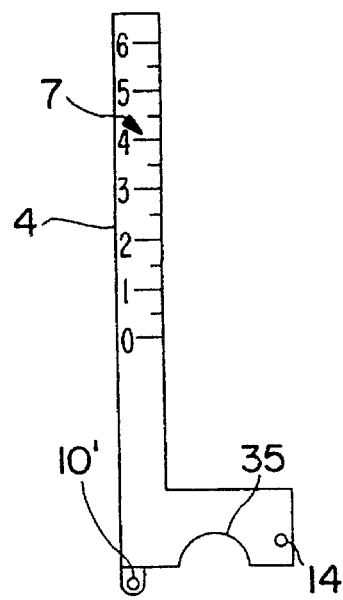
FIG. 4 is a planar view of the distal face of the main body of the insertion guide.
Figure 5:
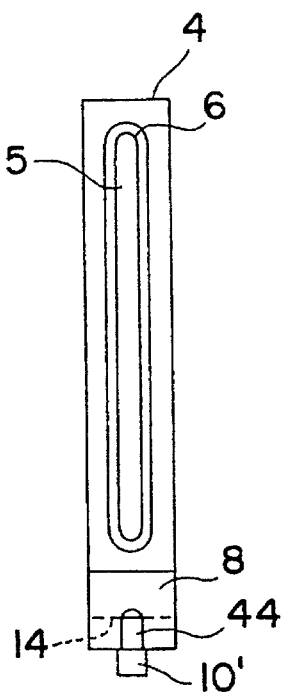
FIG. 5 is a planar view of the inner face of the main body of the insertion guide.
Figure 10:
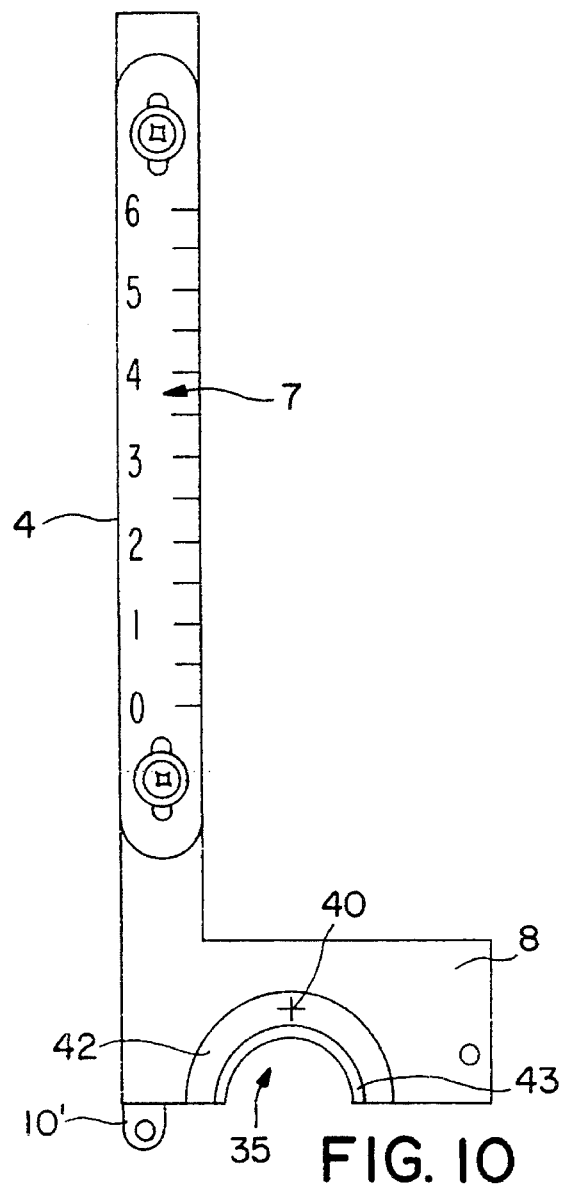
FIG. 10 is a planar view of the distal face of an alternating embodiment of the main body.

The preferred form of main body 3 is shown in FIGS. 4 and 5 which illustrate the distal and inner faces respectively. Anterior-posterior adjustment guide 4 extends upward from first clamp body 8 adjacent one end of first clamp body 8. The appearance, then, of main body 3 is that of an "L" with anterior-posterior adjustment guide 4 forming the upright and first clamp body 8 forming the horizontal leg. Centrally located along the longitudinal axis of anterior-posterior adjustment guide 4 is a slot 5 which passes through adjustment guide 4, from the outside of the "L" to the inside, in line with the longitudinal axis of first clamp body 8. The inner face of guide 4 is relieved along either side of slot 5 to form a slot track 6 which is from ¼ to ½ the depth of slot 5 and about twice the width of slot 5. In the preferred embodiment a measurement scale 7 is located on the distal or rearward face of adjustment guide 4 as shown by FIG. 4. Scale 7 is preferably an integral part of adjustment guide 4 but may be separately fabricated and attached as shown in FIG. 10.

The bottom surface of first clamp body 8 is provided with a semi-circular cutout 35 which extends perpendicularly to the longitudinal axis of adjustment guide 4. Second clamp body 9 is provided with a corresponding semi-circular cut-out 35 in its upper surface so that when clamp bodies 8 and 9 are brought into closed engagement a substantially cylindrical channel 35' is provided within which ultrasound probe 2 is retained. In this manner, insertion guide 1 is removably mountable on ultrasound probe 2 such that adjustment guide 4 extends perpendicularly to the longitudinal axis of probe 2. Cut-outs 35 may be provided in shapes other than semi-circular to accommodate different ultrasound probes 2.

Figure 3:
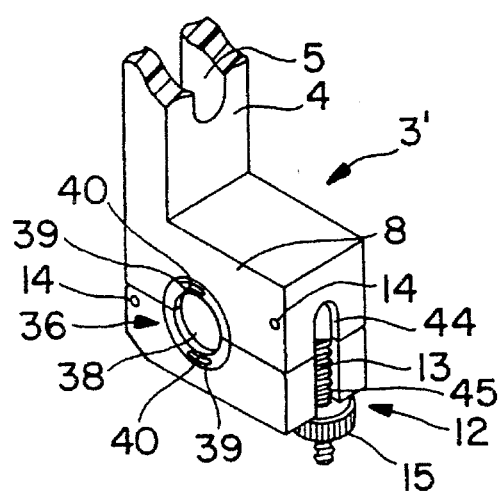
FIG. 3 is a perspective view of the clamp portion of the insertion guide.
Figure 6:
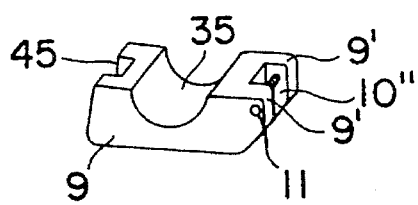
FIG. 6 is a perspective view of the lower clamp member of the insertion guide.

The preferred form of second clamp body 9 as a separate part is shown in FIG. 6. In this embodiment, second clamp body 9 is hingably connected to first clamp body 8 by a hinge 10 which comprises a lug 10' depending from one end of first clamp body 8 and fits into a slot 10" between ears 9' on second clamp body 9. A hinge pin 11 passes through ears 9' and lug 10' to provide a pivot. A latch means 12 is provided on the end of first clamp body 8 opposite hinge 10 to hold clamp bodies 8 and 9 together in a closed relationship about ultrasound probe 2. The preferred form of latch means 12 is shown in FIG. 3 and comprises a pivoting screw post 13 pivotally attached to first clamp body 8 in a recess 44 which allows screw post 13 to pivot through 90°. Second clamp body 9 is provided with a slot 45 which lines up with recess 44 when clamp 3' is closed thereby permitting screw post 13 to pivot into slot 45. Screw post 13 is of sufficient length to extend beyond second clamp body 9 to accept a threaded nut 15 which can be threaded onto screw post 13 and into engagement with second clamp body 9 to hold it closed against first clamp body 8. Although preferably shown with hinge 10 adjacent the lower end of adjustment guide 4 and latch 12 at the opposite end of clamp bodies 8 and 9, this order may be reversed just as the clamp bodies 8 and 9 themselves may be divided vertically as shown in FIG. 16.

Figure 2:
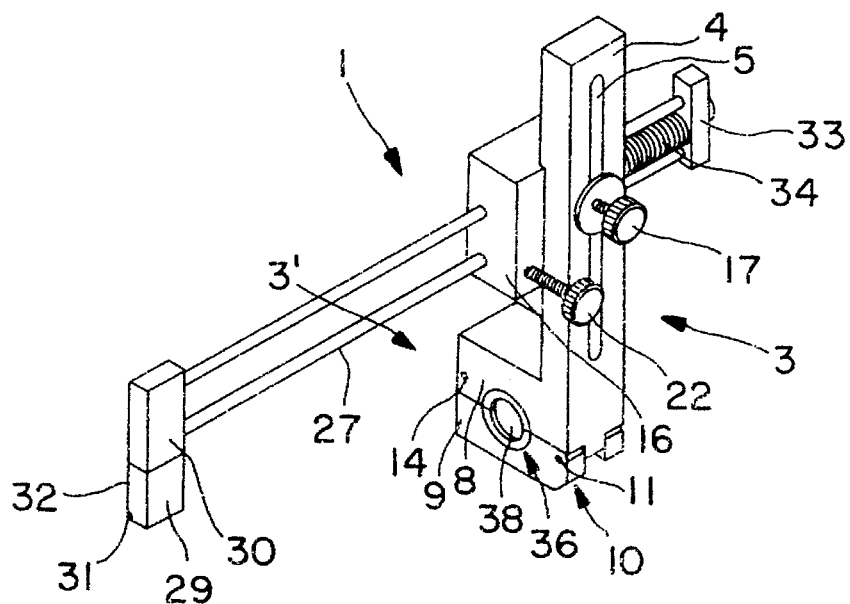
FIG. 2 is a perspective view of a modified form of the insertion guide.
Figure 8:
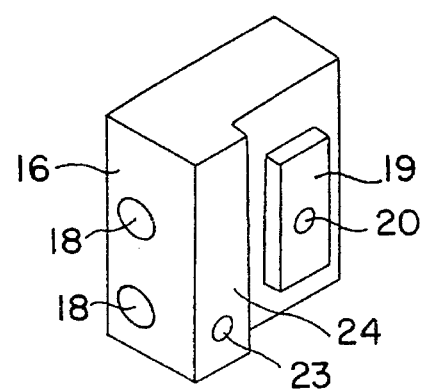
FIG. 8 is a perspective view of the slide block.
Figure 9:
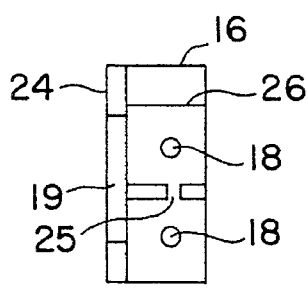
FIG. 9 is a planar view of the distal face of the slide block.

Slidably associated with anterior-posterior adjustment guide 4 is a slide block 16 which provides anterior-posterior positioning adjustment for a biopsy needle relative to ultrasound probe 2. As seen in FIGS. 8 and 9, slide block 16 is designed to cooperate with slot 5 and slot track 6 in adjustment guide 4. To this end, slide block 16 is provided with a track following lug 19 on one face which fits into slot track 6 to guide slide block 16 along adjustment guide 4. Substantially centrally located in track following lug 19 is a threaded hole 20 which accepts the threaded end of a position locking thumb screw 17 which, as is seen in FIGS. 1 and 2, extends through slot 5 to engage slide block 16. Thumb screw 17 is loosened to permit slide block 16 to move along adjustment guide 4 and is tightened against the outer face of adjustment guide 4 to fix slide block 16 in a desired position. Although slide block 16 may be fabricated as a simple rectangular block with track following lug 19, it is preferred that an additional guidance means be provided to steady slide block 16 against adjustment guide 4. This is preferably an extension 24 of slide block 16 which engages the proximal face of adjustment guide 4.

Extending through slide block 16 in a direction parallel to the longitudinal axis of ultrasound probe 2 is at least one channel 18 which slidably receives a needle holder and guide assembly 27. In the illustrated embodiment, a pair of channels 18 are provided to slidably receive the double rod shaft 27' of the needle holder and guide assembly 27. Shaft 27' may be a single rod in which case it should preferably be square to prevent its independent rotation and slide block 16 will only require one channel 18. Depending on the material from which slide block 16 and shaft 27' are manufactured, channels 18 may be provided with lining sleeves 21 to prevent binding of shaft 27' within channels 18. So that needle holder and guide assembly 27 may be fixed in place, slide block 16 is provided with a second threaded hole 23 transverse to and intersecting one of channels 18. Transverse hole 23 receives a second threaded thumb screw 22 which can be tightened against shaft 27' to fix it in a desired position. Loosening thumb screw 22 allows shaft 27' to be slidably repositioned.

Turning to FIG. 9, the distal face of slide block 16 is illustrated. In addition to the distal ends of channels 18, the distal face of slide block 16 is provided with an index mark 26. When insertion guide 1 is assembled, the distal face of slide block 16 is adjacent the distal face of adjustment guide 4 and index mark 26 is read against measurement scale 7 to provide an indication of the measurement which corresponds to the separation between ultrasound probe 2 and a needle held by needle holder and guide assembly 27.

As noted before, needle holder and guide assembly 27 has a shaft 27' which is slidable through channels 18 in slide block 16. In the illustrated embodiment shaft 27' comprises parallel spaced rods. However, shaft 27' may also be a single rod which is preferably square in its cross-sectional shape. Affixed to the distal end of shaft 27' is a rear stop block 33 which provides an attachment point for one end of a tension bias spring 34. The other end of spring 34 attaches to slide block 16 at a point 25 adjacent channels 18. Spring 34 provides tension between needle holder and guide assembly 27 and slide block 16 to ensure that assembly 27 is held firmly against the patient. The stability provided by spring 34 helps to ensure accurate placement of biopsy needles. In the illustrated embodiment, spring 34 is located between the twin rods of shaft 27'. When a single shaft 27' is employed, spring 34 will preferably encompass the distal end of shaft 27' between slide block 16 and rear stop block 33.

Figure 7:
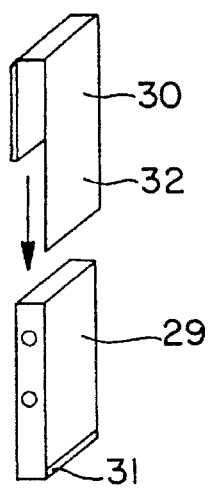
FIG. 7 is a perspective view of the needle holder illustrating the guide block and shield in exploded arrangement.

Affixed to the proximal end of shaft 27' is a needle holder assembly 28 comprising a guide block 29 and a shield 30. Guide block 29 is fixed to the proximal end of shaft 27' and shield 20 fits over guide block 29 as shown in FIG. 7. Guide block 29 depends from shaft 27' toward ultrasound probe 2 and is provided with an elongated notch 31 in one face adjacent the lower end of block 29. Notch 31 is preferably a simple "V" notch and is oriented parallel to the longitudinal axis of shaft 27' and of ultrasound probe 2 to provide guidance for a biopsy needle being inserted. To ensure that the needle is securely held in and guided by notch 31, shield 30 is provided with a spring tab 32 which has sufficient resiliency to allow it to be laterally displaced by insertion of a needle into slot 31 while remaining biased against the needle to hold it in place in slot 31.

FIG. 2 illustrates a modified form of insertion guide 1 wherein the modification permits use of the device on different models of ultrasound probes. In the embodiment of FIG. 1 cut-outs 35 in first and second clamp bodies 8 and 9 are of a fixed size to fit a specific shape and size of ultrasound probes. The modified embodiment of FIG. 2 includes changeable inserts 36 positionable within cut-outs 35 to provide different sizes or shapes of channels 38 in which an ultrasound probe 2 is received and held.

Changeable inserts 36 are illustrated in FIGS. 12–15 and, although the ultimate size and shape of their respective probe channels 38 may differ, inserts 36 have features which are identical regardless of the style of probe 2 they are designed for. Specifically, inserts 36 are provided in two halves to fit clamp bodies 8 and 9. Each half comprises a central body 41 bounded on each side by flanges 37. Preferably central body 41 and flanges 37 are semi-circular to fit in clamp bodies 8 and 9. The channel 38 formed by the two halves of inserts 36 will be of different sizes and/or shapes as shown in FIGS. 13–15 to accommodate different models of ultrasound probes 2. To prevent undue rotation of inserts 36 within clamp bodies 8 and 9 which would lead to inaccurate orientation of insertion guide 1 relative to probe 2, flanges 37 are provided with rotation limiter slots 39 of limited arcuate extent into which limit pins 40 fit. Limit pins 40 are set in clamp bodies 8 and 9 preferably on both sides and may be separate items or they may be formed as an integral part of clamp bodies 8 and 9.

Figure 11:
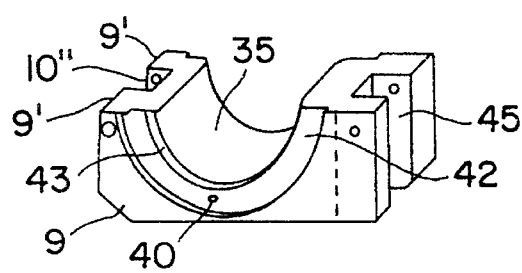
FIG. 11 is a perspective view of an alternative embodiment of the lower clamp member.

Turning to FIGS. 10 and 11, it is seen how clamp bodies 8 and 9 are modified to accept inserts 36. Preferably the faces of clamp bodies 8 and 9 adjacent cut-outs 35 are relieved to form arcuate tracks 42 which receive flanges 37. Limit pins 40 are preferably centrally located in each track 42. The edge of each track 42 adjacent cut-outs 35 may be chamfered as shown at 43. Where insert guide 1 is fabricated of a material to be reusable, such as stainless steel, aluminum, or the like, inserts 36 will preferably be made from a polymer material which as nylon, Delrin or the like and will be removable and replaceable. In this manner, insert guide 1 may be re-used on different models of ultrasound probes 2. Alternatively, where insert guide 1 is fabricated of a material to be disposable, such as nylon, Delrin, polycarbonates, or other polymer materials, it may be specifically manufactured to a particular model of ultrasound probe 2 or it may be modified to accept inserts 36. In the latter case, it may then be necessary to manufacture only one form of insert guide 1 which may be sold with a selection of inserts 36.

As noted previously, insert guide 1 may be manufactured from a variety of metallic and plastic materials. The principal criteria here is that the materials used be sterilizable and sufficiently rigid to hold their shape. Regardless of the material used to manufacture the main body 3, slide block 16 and second clamp body 9, it is preferred that shaft 27, spring 34 and shield 30 be made from metal. Furthermore, where main body 3 and second clamp body 9 are made from a moldable plastic material, they may be molded as an integral unit. In this case hinge 10 and latch 12 may also be molded as integral parts. FIG. 16, in addition to illustrating an alternative arrangement of the clamp bodies 8 and 9, illustrates such an integrally molded unit. With such integral molding, hinge 10 joins second clamp body 9 to first clamp body 8 and is preferably a plastic live hinge. Latch means 12 is also molded as an integral part of clamp 3' and comprises a resilient catch 46 extending from clamp body 8 and a catch detent 48 molded into clamp body 9 in a position to be engaged by resilient catch 46. Preferably catch detent 48 is recessed within a catch channel 47 which receives resilient catch 46 so as to present a flat surface when latch means 12 is engaged. In addition, the end of resilient catch 46 preferably extends beyond the edge of second clamp body 9 to provide a tab whereby resilient catch 46 may be manipulated out of engagement with detent 48 to open and release clamp 3'.

Insert guide 1 finds particular utility in cryosurgical procedures performed on the prostate gland where a rectally inserted ultrasound probe is used to provide an image of the prostate. Insert guide 1 is used in conjunction with the ultrasound probe to accurately place one or more biopsy needles in a patient's prostate with the needles then serving as a means for the insertion of guide wires over which hollow cryoprobe sheaths are then inserted. The sheaths provide access to the prostate for cryogenic probes which are used to freeze the prostate tissue.

In the method for accurate placement of cryoprobes into a human prostate using the insertion guide of this invention, an ultrasound probe is inserted into the patient's rectum and is activated to image the prostate. The extent of the prostate area is measured and locations for placement of cryoprobes are determined. Insert guide 1 is mounted onto ultrasonic probe 2 by clamping probe 2 between first and second clamp bodies 8 and 9 with sufficient force to prevent rotation of insert guide 1 independent of probe 2. Similarly, movement of insert guide 1 along probe 2 should also be prevented. Probe 2 is then reinserted into the patient's rectum and is rotated to position insert guide 1 at the desired angular location for a cryoprobe. Slide block 16 is then positioned along adjustment guide 4 such that index mark 26 is adjacent the desired scale point indicating the anterior-posterior distance between probe 2 and the desired location for the cryoprobe. Slide block 16 is locked in this position with thumb screw 17. At this time, the assembly of the insert guide 1 and probe 2 is advanced proximally until needle holder assembly 28 engages and bears firmly against the patient's perineum. This places spring 34 under tension which serves to maintain needle holder assembly firmly against the perineum. The needle holder and guide assembly 27 is then locked in place by tightening thumb screw 22 against shaft 27'. The surgeon need then only maintain a firm grip and slight proximal pressure on ultrasound probe 2 to keep insert guide 1 in position thereby providing a firm and stable guide for the insertion of a biopsy needle.

A biopsy needle is placed in notch 31 between guide block 29 and spring tab 32 and is held there by spring tab 32. The surgeon may then advance the needle into the patient while observing its progress on an ultrasound image monitor. The combination of the firm engagement of the perineum by needle holder assembly 28 and the fixation of insert guide 1 to ultrasound probe 2 provides a stable guide for accurate insertion of biopsy needles into the prostate. When the needle is in place it is disengaged from needle holder assembly 28 by releasing spring tab 32 and insert guide 1 can be re-positioned to insert additional needles.

When all needles have been positioned, insert guide 1 is removed from probe 2 by releasing latch 12 to separate clamp bodies 8 and 9. Guide wires are then inserted through the needles and the needles withdrawn leaving the guide wires in place. Cryoprobe sheaths with obturators are inserted into the prostate over the guide wires which are then removed along with the obturators leaving the cryoprobe sheaths in place. A cryoprobe is inserted into each sheath and is activated to freeze the prostate. As with the insertion of the needles, placement of the guide wires, cryoprobe sheaths, cryoprobes and the freezing process are observed by means of the ultrasound image. When the freezing process has been completed, the cryoprobes are allowed to thaw before they are removed, along with the sheaths, and the puncture wounds are closed, preferably with one or two sutures.

The inventors herein have described an improved biopsy needle insertion guide and a method of use whereby biopsy needles and cryoprobes can be accurately placed in internal organs relative to an ultrasound probe. Although the invention has been described in connection with a preferred embodiment, the description is not intended to limit the invention. It is the intention of the appended claims to cover any and all changes and modifications which may be made by, or become apparent to, one or ordinary skill in the art without departing from the spirit and scope of the invention or sacrificing any of its material advantages.

What is claimed is:

1. A biopsy needle insertion guide for use with an elongated ultrasound probe in medical procedures, the guide comprising (a) a body removably mountable on an ultrasound probe and comprising a clamp affixable about said probe and an elongated adjustment guide extending from said clamp in a direction perpendicular to said probe when said body is mounted thereon;

(b) a slide block engaging said adjustment guide and slidably adjustable therealong; and (c) a needle holder and guide assembly carried by said slide block and extendable from said slide block in a direction parallel to said probe when said body is mounted thereon.

2. The biopsy needle insertion guide of claim 1 wherein said needle holder and guide assembly is slidably adjustable relative to said slide block.

3. The biopsy needle insertion guide of claim 2 further comprising a screw member to lock said slide block in a fixed position relative to said adjustment guide.

4. The biopsy needle insertion guide of claim 3 further comprising a screw member to lock said needle holder and guide assembly in a fixed position relative to said slide block.

5. The biopsy needle insertion guide of claim 4 wherein said needle holder and guide assembly comprises an elongated shaft slidably held by said slide block and extendable therefrom in a direction perpendicular to said adjustment guide and parallel to said ultrasonic probe when said body is mounted on said probe; and a needle holder attached to the proximal end of said shaft and oriented to provide guidance for a biopsy needle in a direction substantially parallel to said probe.

6. The biopsy needle insertion guide of claim 5 further comprising a rear stop block on the end of said shaft opposite to said needle holder and a biasing spring between said rear stop block and said slide block whereby said needle holder and guide assembly is biased in a proximal direction relative to said probe.

7. The biopsy needle insertion guide of claim 6 wherein said slide block is provided with at least one channel therethrough through which said shaft passes and within which said shaft is slidable, said at least one channel having an orientation perpendicular to said adjustment guide and parallel to said probe when said body is mounted on said probe.

8. The biopsy needle insertion guide of claim 5 further comprising a measuring scale along said elongated adjustment guide and a position indicator on said slide block adjacent said measuring scale, said position indicator being located on said slide block whereby a measurement on said scale indicated by said position indicator corresponds to the position of a needle in said needle holder relative to said ultrasonic probe.

9. The biopsy needle insertion guide of claim 8 wherein said needle holder comprises a needle guide block attached to the proximal end of said shaft and a shield member affixable to said guide block.

10. The biopsy needle insertion guide of claim 9 wherein said needle guide block is provided with an elongated notch in one surface of said guide block extending thereacross and parallel to said shaft and said shield comprises a tab extending over said notch, whereby said tab serves as a biased retention member to hold a biopsy needle in said notch between said guide block and said tab.

11. The biopsy needle insertion guide of claim 1 wherein said clamp comprises a first clamp member from which said elongated adjustment guide extends, a second clamp member hingably connected to said first clamp member to permit opening and closing of said clamp, hinge means between said first and second clamp members, and latch means to hold said clamp in a closed condition about said ultrasound probe, said clamp members cooperating to provide a channel within which said probe is retained.

12. The biopsy needle insertion guide of claim 11 wherein said hinge means comprises interfitting lug and ears on said clamp members and a pivot pin connecting said members through said lug and ears.

13. The biopsy needle insertion guide of claim 11 wherein said hinge means comprises an integral live hinge connecting said clamp members.

14. The biopsy needle insertion guide of claim 11 wherein said latch means comprises a screw post pivotally connected to said first clamp member and capable of engaging a slot in said second clamp member and a nut threadable on said screw post whereby said screw post has a length to extend beyond said second clamp member when engaged in said slot and said nut is threadable against said second clamp member to hold said first and second clamp members in closed engagement.

15. The biopsy needle insertion guide of claim 11 wherein said latch means comprises an integral spring catch on one clamp member and a cooperating detent on the other clamp member.

16. The biopsy needle insertion guide of claim 11 further comprising changeable insert members positionable within said clamp whereby said guide is adaptable to fit different ultrasonic probes.

17. A biopsy needle insertion guide for use with an elongated ultrasound probe insertable into body orifices in medical procedures the guide comprising:

(a) a first body having a first portion with a semicircular cut-out therein forming a first clamp member and a second elongated portion extending from said first portion opposite said cutout, said second portion having a longitudinal slot therein;

(b) a second body forming a second clamp member hingeably connected to said first portion of said first body and having a semicircular cut-out therein whereby, when said second body is brought into mating engagement with said first portion of said first body, said semicircular cut-outs cooperate thereby forming a through channel in which said ultrasound probe is receivable, said through channel having a longitudinal axis perpendicular to said longitudinal slot;

(c) hinge means connecting said second body to said first portion of said first body and latch means to latch said second body and said first portion of said first body in a clamping arrangement about said ultrasound probe;

(d) a third body slidable within said slot in said second portion of said first body; and (e) a needle guide assembly adjustably carried by said slidable third body and comprising an elongated shaft extendable through said slidable third body in a direction parallel to the longitudinal axis of said clamp through channel, a needle holder on a first end of said shaft and a biasing spring connected between said slideable third body and a second end of said shaft;

whereby said clamp members cooperate to removably and rigidly mount said insertion guide onto said ultrasound probe whereby said elongated shaft is parallel to the longitudinal axis of said probe, said elongated portion of said first body extends in a direction perpendicular to the longitudinal axis of said probe such that said third body is slidable along said elongated portion toward and away from said probe, and said needle guide assembly is slidable parallel to said probe whereby a biopsy needle held by said needle holder is variably positionable for entry into a body at positions radially located relative to said probe.

18. The biopsy needle insertion guide of claim 17, further comprising screw members to lock said slide block and said needle guide assembly into fixed positions relative to said probe.

19. The biopsy needle insertion guide of claim 18, further comprising changeable inserts positionable within said clamp through channel, whereby said guide is modified to fit different models of ultrasound probes.

20. The biopsy needle insertion guide of claim 19 further comprising a position measuring scale on said elongated portion of said first body and a position indicator on said slidable third body adjacent to said scale whereby said position indicator is located on said slidable third body such that the point in said scale designated by said indicator corresponds to the distance between said probe and a biopsy needle held by said needle holder.

21. A method for accurate placement of cryoprobes into a human prostate during prostate cryosurgery wherein a rectally inserted elongated ultrasound probe is employed for imaging the prostate, the method comprising the steps of:

(a) providing a biopsy needle insertion guide removably mountable to said ultrasound probe and comprising a clamp for mounting said guide to said probe, an elongated adjustment guide extending from said clamp in a direction perpendicular to said probe, a slide block engaging said adjustment guide and slidably adjustable therealong, and a biopsy needle holder and guide assembly carried by said slide block and extendable therefrom in a direction parallel to said probe;

(b) mounting said biopsy needle insertion guide on said ultrasonic probe whereby said probe is insertable into a patient's rectum and said biopsy needle holder and guide is extendable toward a proximal end of said probe to engage patient's perineum;

(c) inserting said probe into a patient's rectum and activating ultrasound imaging means whereby said prostate is imaged;

(d) adjusting said slide block along said adjustment guide to a position relative to said probe corresponding to a desired needle insertion point as determined from the ultrasound image of said prostate;

(e) advancing said probe and insert guide proximally to engage the patient's perineum with said biopsy needle and holder;

(f) inserting a biopsy needle through said needle guide and holder into said prostate;

(g) inserting a guide wire through said needle;

(h) removing said needle and insertion guide while leaving said ultrasound probe and guide wire in place;

(i) inserting a cryoprobe sheath over said guide wire followed by removal of said guide wire; and (j) inserting a cryoprobe through said sheath into said prostate;

whereby said cryoprobe is accurately positioned in said prostate and is activated to freeze said prostate.

22. The method of claim 21 wherein said biopsy needle insertion guide further comprises screw members whereby said slide block and needle holder and guide assembly are fixed into position following adjustment thereof.

23. The method of claim 22 further comprising the steps of repositioning said biopsy needle insertion guide relative to said ultrasound probe, inserting additional biopsy needles into said prostate at selected locations determined by observation of said ultrasound image, placing guide wires through said needles, removing said needles and inserting a cryoprobe sheath over each guide wire, whereby a plurality of cryoprobes are positionable at said selected locations within said prostate.

* * * * *